United States Patent [19]

Shakkottai et al.

[11] Patent Number: 5,159,843
[45] Date of Patent: Nov. 3, 1992

[54] ACOUSTIC DEVICE AND METHOD FOR MEASURING GAS DENSITIES

[75] Inventors: Parthasarathy Shakkottai, Duarte; Eug Y. Kwack, Walnut; Lloyd Back, La Canada, all of Calif.

[73] Assignee: The United States of America as represented by the Administrator of the National Aeronautics and Space Administration, Washington, D.C.

[21] Appl. No.: 658,477

[22] Filed: Feb. 19, 1991

[51] Int. Cl.⁵ .................... G01N 29/00; G01N 29/22
[52] U.S. Cl. ................................ 73/24.05; 73/24.06; 73/24.01
[58] Field of Search ............... 73/24.01, 24.05, 23.21, 73/24.06, 32 A

[56] References Cited

U.S. PATENT DOCUMENTS

| | | |
|---|---|---|
| 2,963,899 | 12/1960 | Martin et al. ................ 73/24.01 |
| 3,468,157 | 9/1969 | Burke et al. ................ 73/24.01 |
| 3,762,197 | 10/1973 | Roof et al. ................ 73/24.01 |
| 3,789,655 | 2/1974 | Passeri ................ 73/24.01 |
| 4,882,931 | 11/1989 | Breeuwer ................ 73/189 |

FOREIGN PATENT DOCUMENTS 2456510  8/1976  Fed. Rep. of Germany ..... 73/24.01

OTHER PUBLICATIONS

E. N. Haran, Rev. Sci. Instrum. 59,2059 (1988).
L. P. Landau and E. M. Lifshitz, Fluid Mechanics, Pergamon Press, London.

Primary Examiner—Hezron E. Williams
Assistant Examiner—Michael J. Brock
Attorney, Agent, or Firm—Thomas H. Jones; John R. Manning; Guy M. Miller

[57] ABSTRACT

Density measurements can be made in a gas contained in a flow through enclosure by measuring the sound pressure level at a receiver or microphone located near a dipole sound source which is driven at constant velocity amplitude at low frequencies. Analytical results, which are provided in terms of geometrical parameters, wave numbers and sound source type for systems of this invention, agree well with published data. The relatively simple designs feature a transmitter transducer at the closed end of a small tube and a receiver transducer on the circumference of the small tube located a small distance away from the transmitter. The transmitter should be a dipole operated at low frequency with the kL value preferably less than about 0.3.

27 Claims, 10 Drawing Sheets

ACOUSTIC DEVICE AND METHOD FOR MEASURING GAS DENSITIES

ORIGIN OF INVENTION

The invention described herein was made in the performance of work under a NASA contract, and is subject to the provisions of Public Law 96-517 (35 USC 202) in which the Contractor has elected not to retain title.

TECHNICAL FIELD

The invention relates to devices for the measurement of gas densities using an acoustical sensor system and is useful for determination of gas density both in an enclosed vessel and on-line.

BACKGROUND OF THE INVENTION

It would be useful to have a sensor to measure the density of a gas or a mixture of gases in chemical and physical processes. Density is normally not measured for gased because there are no simple methods to sense density directly. Optical interferometry can be used but this is not simple for process control applications. One technique is to measure the acoustic wave transmitted in an enclosure as proposed by Haran, Tech. Mess. 50, 43 (1983). In Haran's analysis, the pressure at the receiver located opposite a transmitter driven at a fixed velocity amplitude, is proportional to the gas density only. However, the measurements of eight different gases did not show linearity with gas density. The assumption by Haran that there exist plane waves with pressure nodes at x=0, i.e. transmitter, a requirement for linearity in density, we believe is faulty.

More recently, an acoustic method to measure gas density has been proposed in which sound produced by a transducer is detected a small distance away by another transducer; see Haran, Rev. Sci. Instrum. 59, 2059 (1988). Under proper conditions, this concept can be used to measure on-line gas density. An analysis of such proper conditions are discussed below in which our analysis shows that dipole-type sources in small enclosures, operated at low frequencies, can provide low-cost, effective, density measurement cells. We also show that a small tube driven by sources at the closed ends in opposite phases with a microphone located a short distance sway from one source also produces a density measurement cell of convenient design.

SUMMARY OF THE INVENTION

It is an object of this invention to provide an on-line sensor to measure the density of a gas or a mixture of gases in chemical and physical processes. We have shown that this objective can be achieved with a simple tube open at one end and driven by a sound source at the opposite closed end. The signal is detected a short distance from the source thereby providing a density measurement system when the open end is not present in a confined volume. In flowing systems and systems that are open to the atmosphere, the wave that leaves the open end does not return and a simple tube can be used as a density sensor.

Figure 14:
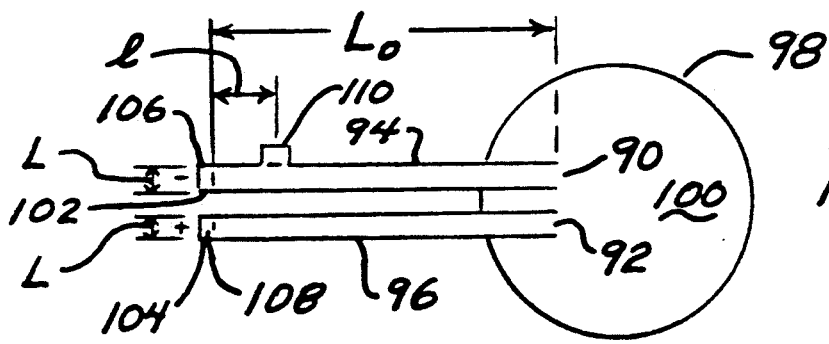
FIG. 14 illustrates a dipole-like sensor system for determination of gas density in a closed volume.

In general, two tubes located side by side and driven by sources in opposite phase constitute a dipole with the sound pressure being measured in one of the tubes, see FIG. 14. In another embodiment of this invention the two tubes are joined by making the open ends touch each other thereby forming a closed tube having the same pressure-density relationship as an open end single tube. Such tubular density cells and method of use provide a novel way of measuring, on-line, fluid densities in a flow stream.

Figure 1:
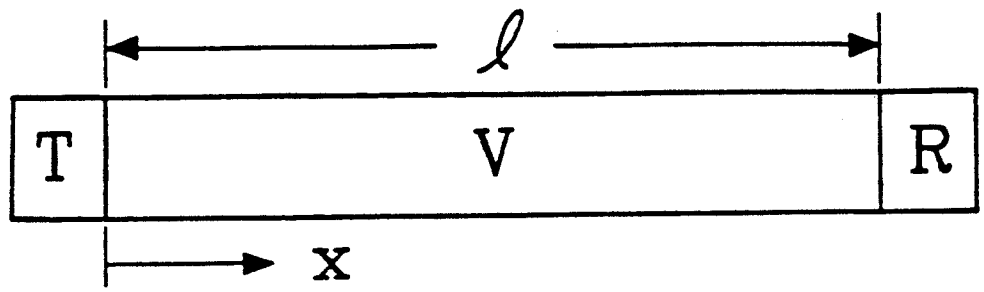
FIG. 1 is a schematic diagram for producing plane wave motion in a closed tube with the transmitter and receiver located at the tube ends.

To ascertain requirements for a gas density sensor it is helpful to first consider a very simple case wherein the transmission and reception of sound occurs in a tube wherein the gas having density $\rho$ is trapped within a small tube as depicted in FIG. 1. The transmitter generates a sound wave having velocity $u_o$ at frequency $\omega$ or wave number k and produces a pressure p in the form of a standing wave, wherein $$p(x) = \rho c u_o e^{-i\omega t}(e^{ikx} + e^{2ikl - ikx})/(1 - e^{2ikl}), \quad \text{(Eq. 1)}$$

where c is the speed of sound in the gas. Equation 1 at $x = l$ gives, $$p(l) = (2\rho c u_o e^{-i\omega t + ikl})/(1 - e^{2ikl}). \quad \text{(Eq. 2)}$$

The pressure therefore depends on $\rho c$ and kl when $\omega$ and $u_o$ are fixed. As $kl \to 0$, i.e. $k \to 0$, $$p(l) = 2\rho c u_o e^{-i\omega t}/(-2ikl) = i\rho c^2 u_o e^{-i\omega t}/(l\omega). \quad \text{(Eq. 3)}$$

In this case, for fixed $\omega$ and $u_o$, p(l) varies as $\rho c^2$. Therefore, this type of cell cannot be used as a density sensor. This cell design naturally involves compressibility and hence the speed of sound, c. In this case, the trapped gas in the volume V undergoes compressions and rarefactions and produces a dependence $\sim(kl)^{-1}$ in the expression for p(l). Eq. 3 is similar to the corresponding one for a piston phone which is used to calibrate microphones.

Figure 2:
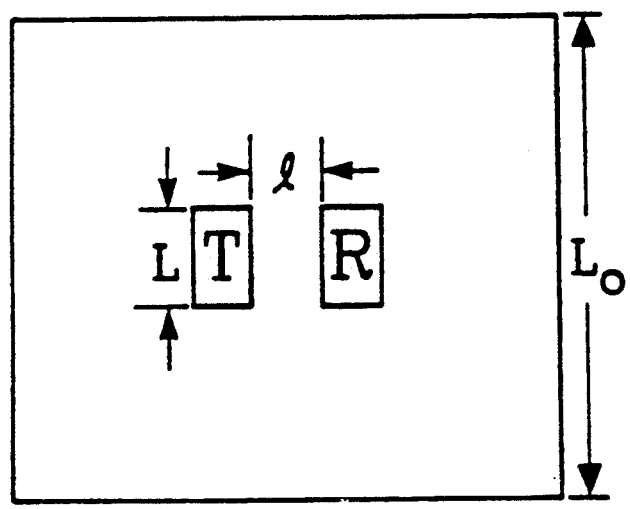
FIG. 2 is a schematic diagram of a transmitter and receiver separated by a small distance located in an enclosure for producing a dipole-like flow field near the transmitter.

Next the case of the transmitter and receiver enclosed within a volume containing the chosen gas was considered as depicted in FIG. 2. Transmitter T and receiver R, both having characteristic size L, are separated by a distance l. The enclosing vessel has a larger length $L_o$. We expect from dimensional analysis that $$p/\rho c u_o = F(kL, kl, kL_o). \quad \text{(Eq. 4)}$$

To find out more about this function, the following simpler geometry was considered. The pressure generated at a point on the surface of a pulsating sphere, i.e. a monopole, of radius R in an infinite medium is given by Landau and Lifshitz, Fluid Mechanics, Pergamon Press, London, 1959, pages 284–285 as $$|p/\rho c u_o| = kR/(1 + k^2 R^2)^{0.5}. \quad \text{(Eq. 5)}$$

Figure 3:
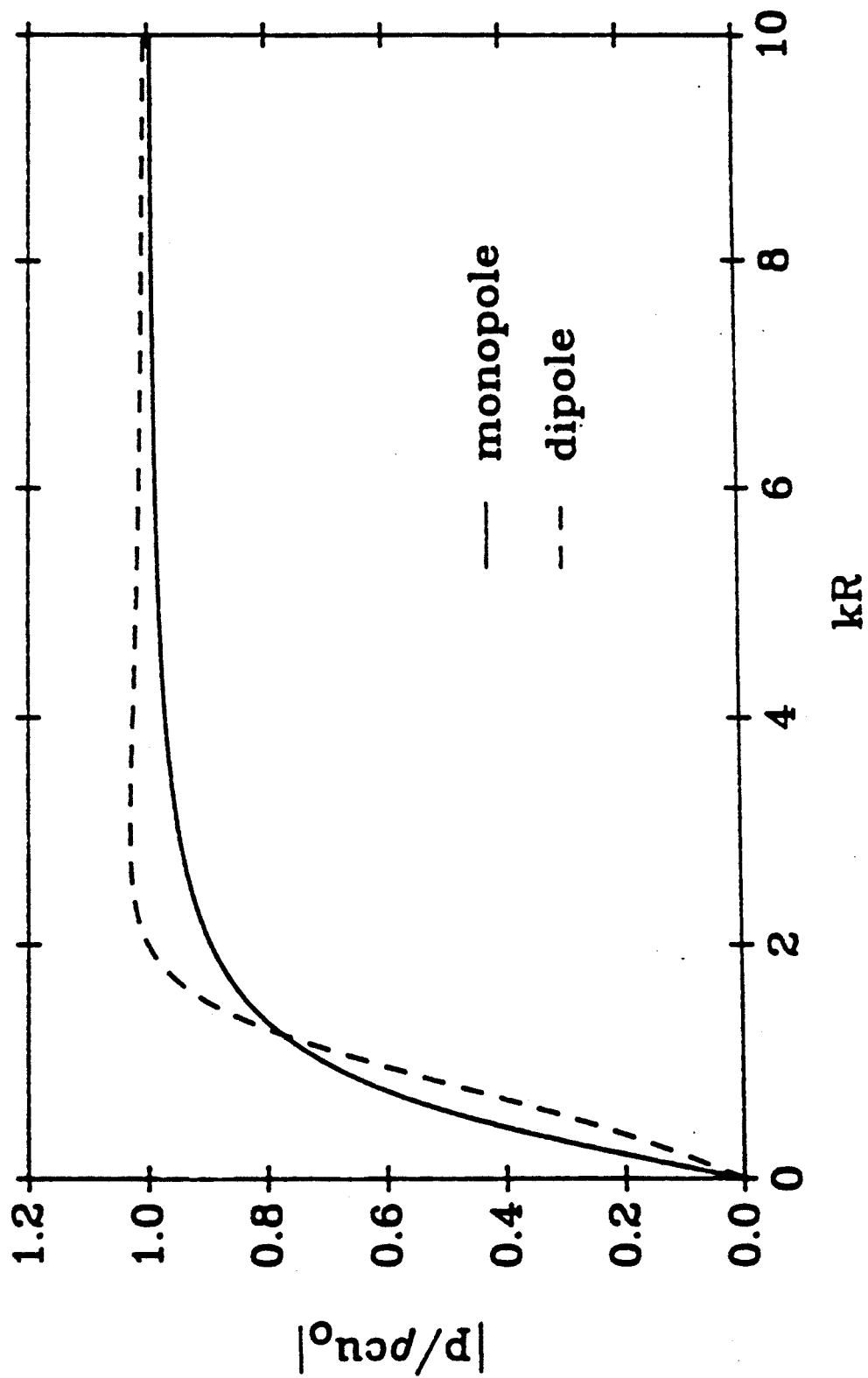
FIG. 3 is a graph of $|p/\rho c u_o|$ as a function of the wave number parameter $kR$ generated by pulsating (monopole) and oscillating (dipole) spheres at fixed velocity amplitude $u_o$.

Similar results are valid at points near the sphere. For an oscillating sphere, i.e. a dipole, the result is $$|p/\rho c u_o| = kR \, (k^2 R^2 + 1)^{0.5}/(k^4 R^4 + 4)^{0.5}, \quad \text{(Eq. 6)}$$

at polar coordinates $r = R$ and $\theta = 0$. Both of these functions are seen in FIG. 3 to be linear at small kR and to saturate at unity as kR approaches infinity. If $p/\rho c u_o$ is linear in kR, $p \sim \rho \omega u_o R$. Therefore, it would appear that density measurements can be made at a sufficiently small value of kR using an oscillating or pulsating body in a gaseous medium. However, the effect of enclosing the oscillating or pulsating body makes the results differ greatly from each other.

Next the case of a sphere of radius R oscillating inside another sphere of radius $R_o$ was considered. This geometry has a potential $$\phi = u \cdot \nabla(Ae^{ikr}/r + Be^{-ikr}/r)e^{-i\omega t}, \quad \text{(Eq. 7)}$$

with $$B = -Ae^{2ikR_o} g(kR_o)/h(kR_o), \quad \text{(Eq. 8)}$$

$$A = (R^3 e^{-ikR})/D, \quad \text{(Eq. 9)}$$

where $$g(kr) = -k^2 r^2 - 2ikr + 2, \quad \text{(Eq. 10A)}$$

and $$h(kr) = -k^2 r^2 + 2ikr + 2, \quad \text{(Eq. 10B)}$$

with $$D = g(kR) - [h(kR)g(kR_o)\{e^{2ik(R_o - R)}\}/h(kR_o)]. \quad \text{(Eq. 11)}$$

Figure 4:
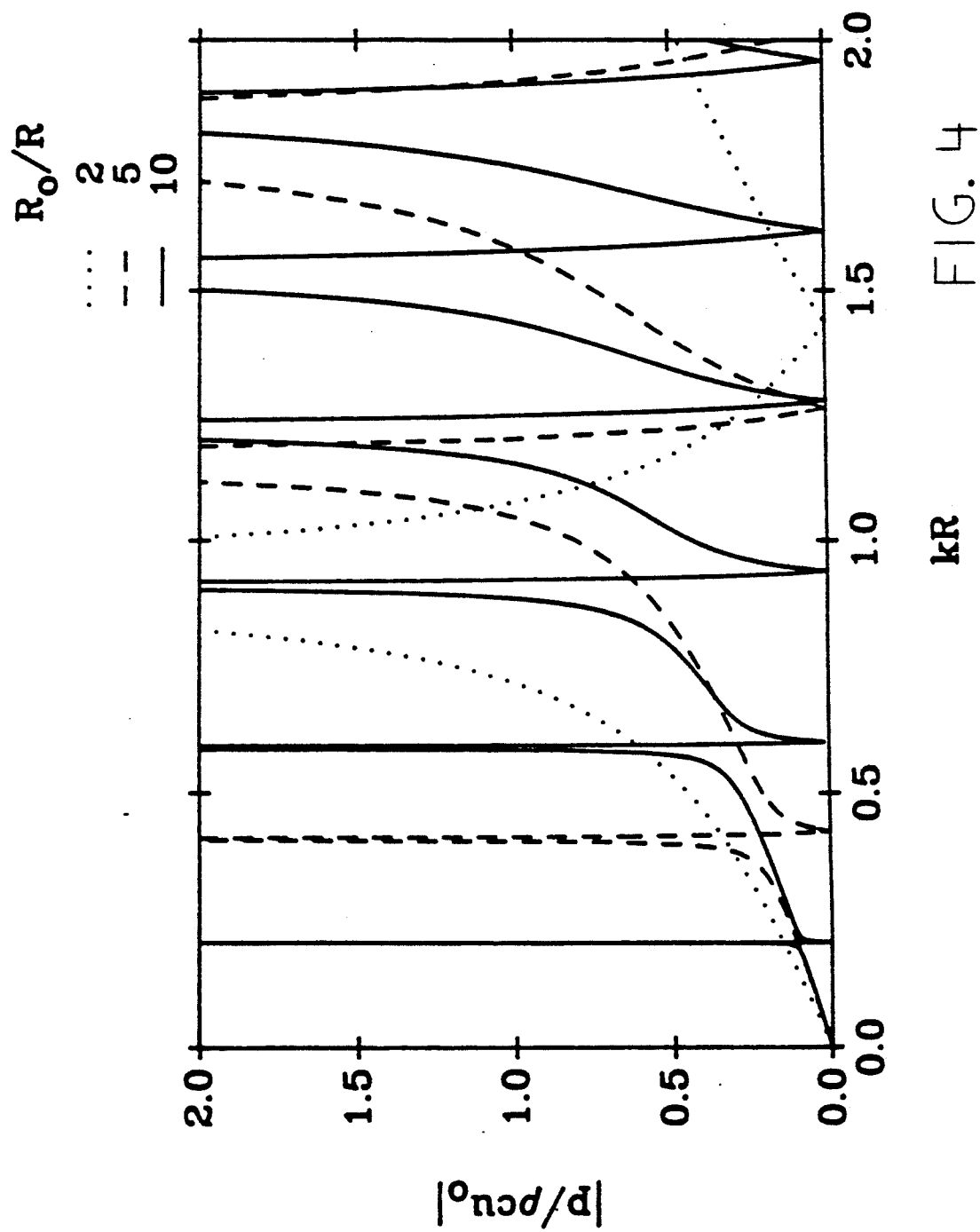
FIG. 4 is a graph of $|p/\rho c u_o|$ as a function of $kR$ for an oscillating sphere (dipole) of radius R enclosed in an outer sphere of radius $R_o$ at several ratios of $R_o/R$ which shows the linear region near zero and the periodic resonances produced by such geometry.

The solutions for the magnitude of surface pressure at polar coordinates $r = R$, $\theta = 0$ which is equal to $|i\rho\omega\phi|$, are calculated for values of $R_o/R$ equal to 2, 5 and 10 and are shown plotted in FIG. 4 as the dimensionless pressure parameter $|p/\rho c u_o|$ versus kR. The pressure parameter is linear in kR for $kR < 0.3$ when $R_o/R$ is not large. Therefore, a density measurement cell can be constructed with a suitable choice of $R_o/R$. If $R_o/R$ is large, resonances appear at $k(R_o - R) = N\pi$ for integral values of N. The first resonance will appear at a low value of kR which is undesirable. Therefore $R_o/R$ should not be chosen to be too large.

For the case of a pulsating sphere contained in an enclosing sphere, the potential is found to be $$\phi = (Ee^{ikr}/r + Fe^{-ikr}/r) \, e^{-i\omega t}, \quad \text{(Eq. 12)}$$

where $$E = [u_o R^2 e^{-ikR}]/[G \, (1 + ikR)], \quad \text{(Eq. 13)}$$

$$F = Ee^{2ikR_o} (ikR_o - 1)/(ikR_o + 1), \quad \text{(Eq. 14)}$$

$$G = [(ikR - 1)/(ikR + 1)] - [e^{2ik(R_o - R)}(ikR_o - 1)/(ikR_o + 1)] \quad \text{(Eq. 15)}$$

with $$p(R) = |i\omega\rho\phi(R)|. \quad \text{(Eq. 16)}$$

Figure 5:
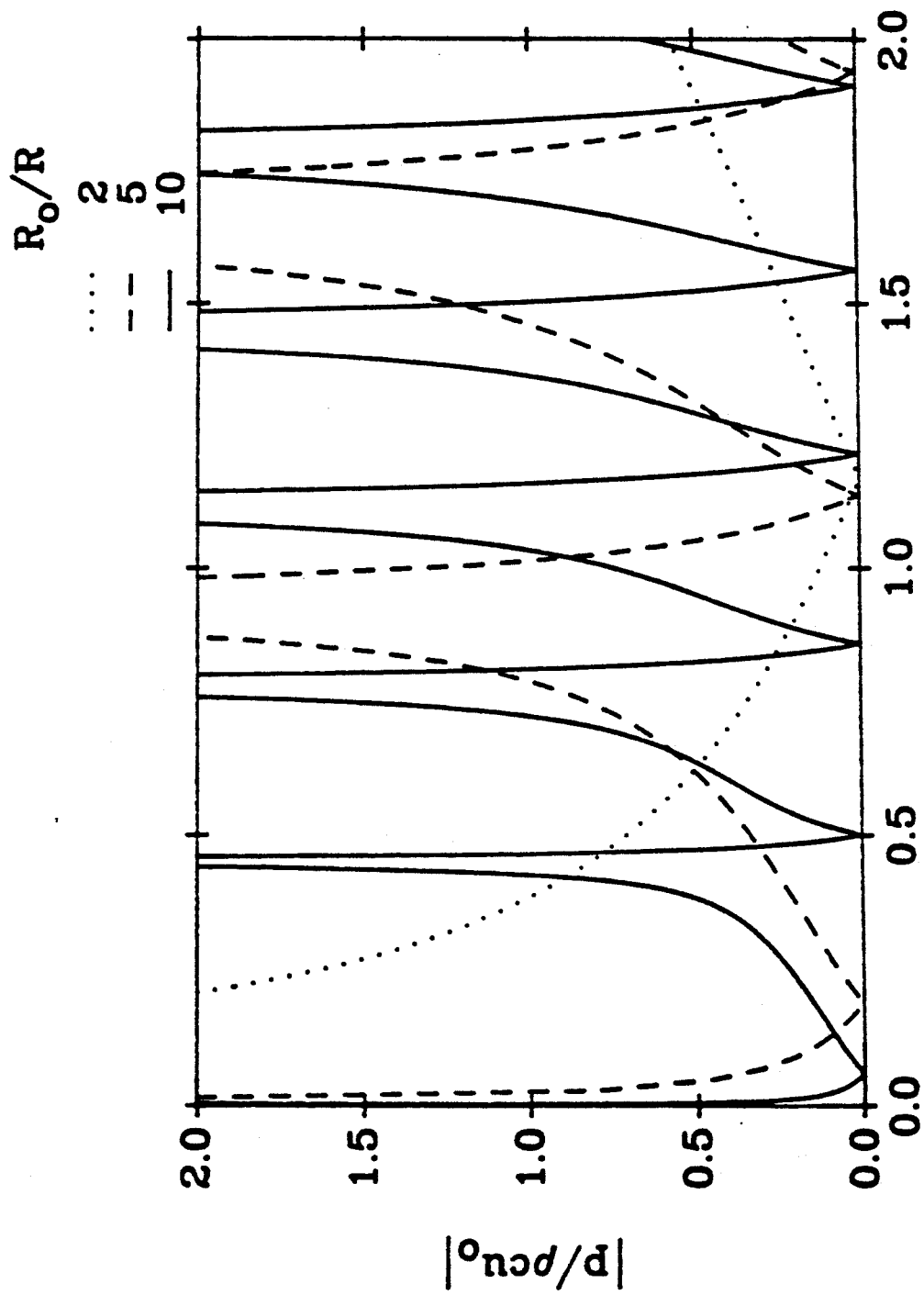
FIG. 5 is a graph of $|p/\rho c u_o|$ as a function of $kR$ for a pulsating sphere (monopole) of radius R enclosed in an outer sphere of radius $R_o$ at several values of the ratio $R_o/R$ which shows the absence of a linear region near $kR=0$ and the multiple resonances produced by such geometry.

As in the last example $|p/\rho c u_o|$ is plotted versus kR for $R_o/R$ equal to 2, 5 and 10 in FIG. 5. It is immediately clear that there is no linear region. The decrease from infinity shows a typical piston phone behavior where $p \sim (kR)^{-1}$.

The effect of l, the distance between the transmitter and receiver was not analyzed because it was easier to analyze a simpler geometry with plane wave motion. For example, a sound source at the closed end ($x = 0$) of a pipe, open at its opposite end ($x = L_o$), with a receiver along the sidewall at $x = l$. In this geometry, $$p(x) = \rho c u_o e^{-i\omega t} \, [e^{ikx} - e^{(2ikL_o - ikx)}]/[1 + e^{2ikL_o}]. \quad \text{(Eq. 17)}$$

Figure 6:
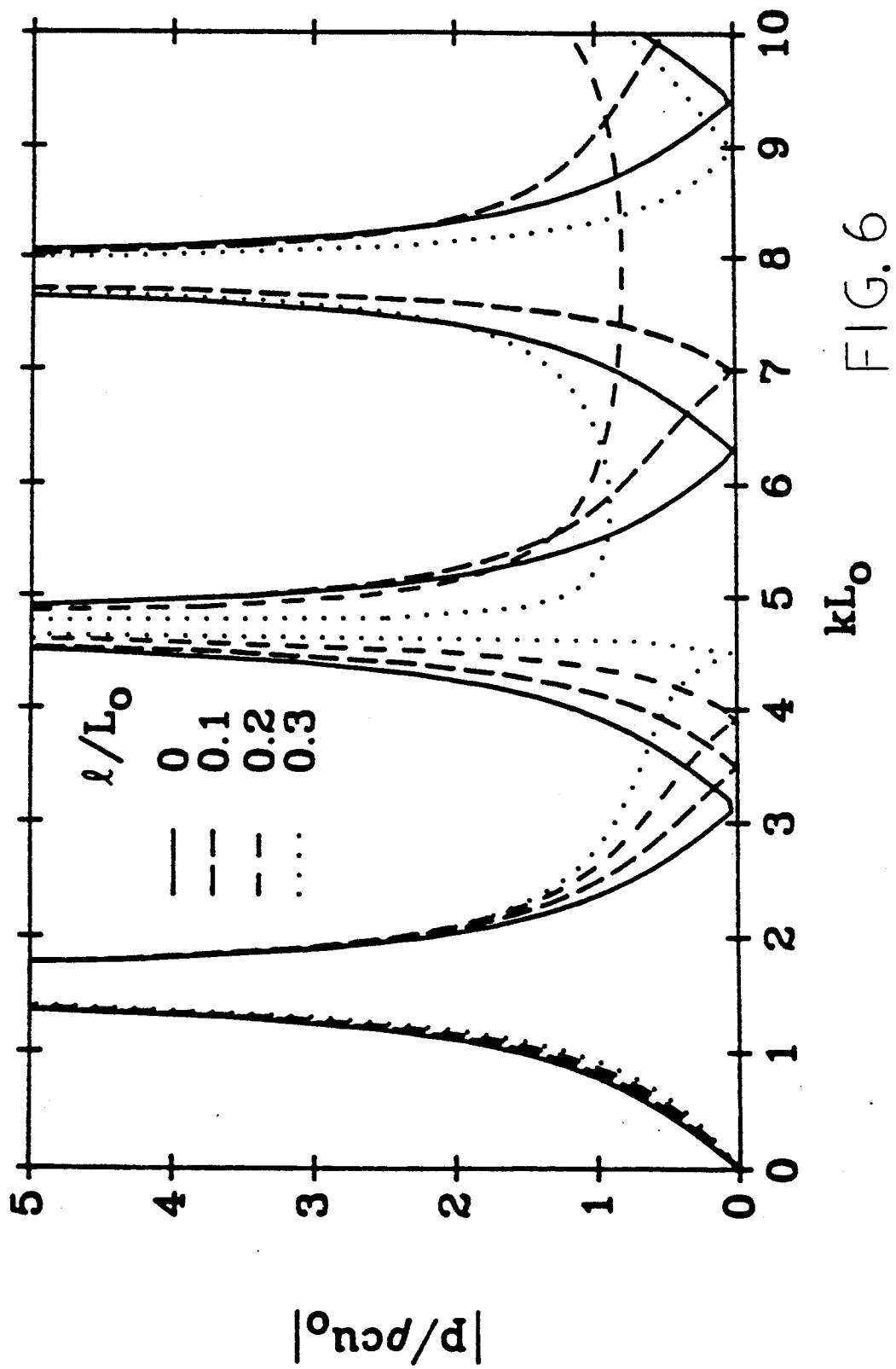
FIG. 6 is a graph of $|p/\rho c u_o|$ as a function of $kL_o$ for an open tube of length $L_o$ driven at its closed end by a pressure transmitting source, with the pressure being detected at varying distances l from the source. The linear region near $kL_o=0$ is similar to that of an enclosed dipole.

The parameter $|p(l)/\rho c u_o|$ is shown as a function of $kL_o$ in FIG. 6 which evidences a linear region for which $p \sim \rho u_o \omega L_o$ at $kL_o$ values near zero, and periodic resonances for the dipole-like solution. The effect of l is seen to be insignificant and any small value such as $1/L_o=0.3$ will suffice.

We next considered the experimental data by Haran mentioned above. Two different cells were used by Haran, and the two cells exhibit different behavior. The densities of eight different gases were determined by Haran by measuring the alternating pressure of an acoustic field set up in the gases in a prototype cell, see Table 1. Characteristics of a prototype cell were reported as cell output as a function of gas density using the several different gases designated in FIG. 7. It can be seen that the cell output is not linear with gas density $\rho$. Haran attributed this nonlinearity to the existence of gas cushions behind the transmitter and between the diaphragm and receiver back electrode. We, however, believe that the output depends not only on $\rho$ but also on $kL$, $kL_o$ and $kl$ as shown in Eq. 4.

Figure 7:
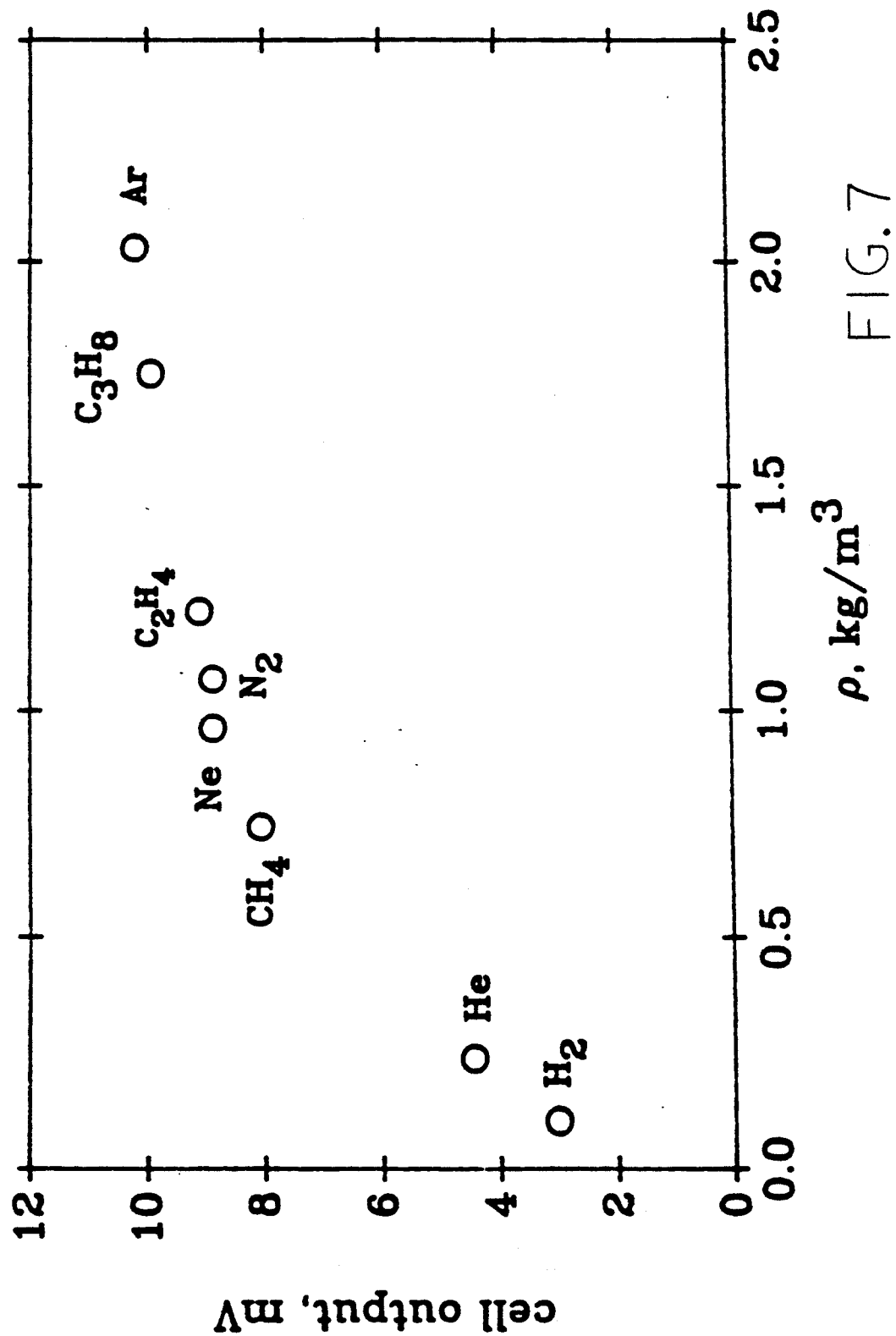
FIG. 7 is a reproduction of a graph that was published in Rev. Sci. Instrum., Vol. 59, No. 9, 2060 (1988) of data acquired by Haran using a density measurement prototype cell, of cell output as a function of gas density for several gases using frequencies from 200–450 Hz. The graph illustrates that these functions have a non-linear relationship.
Figure 8:
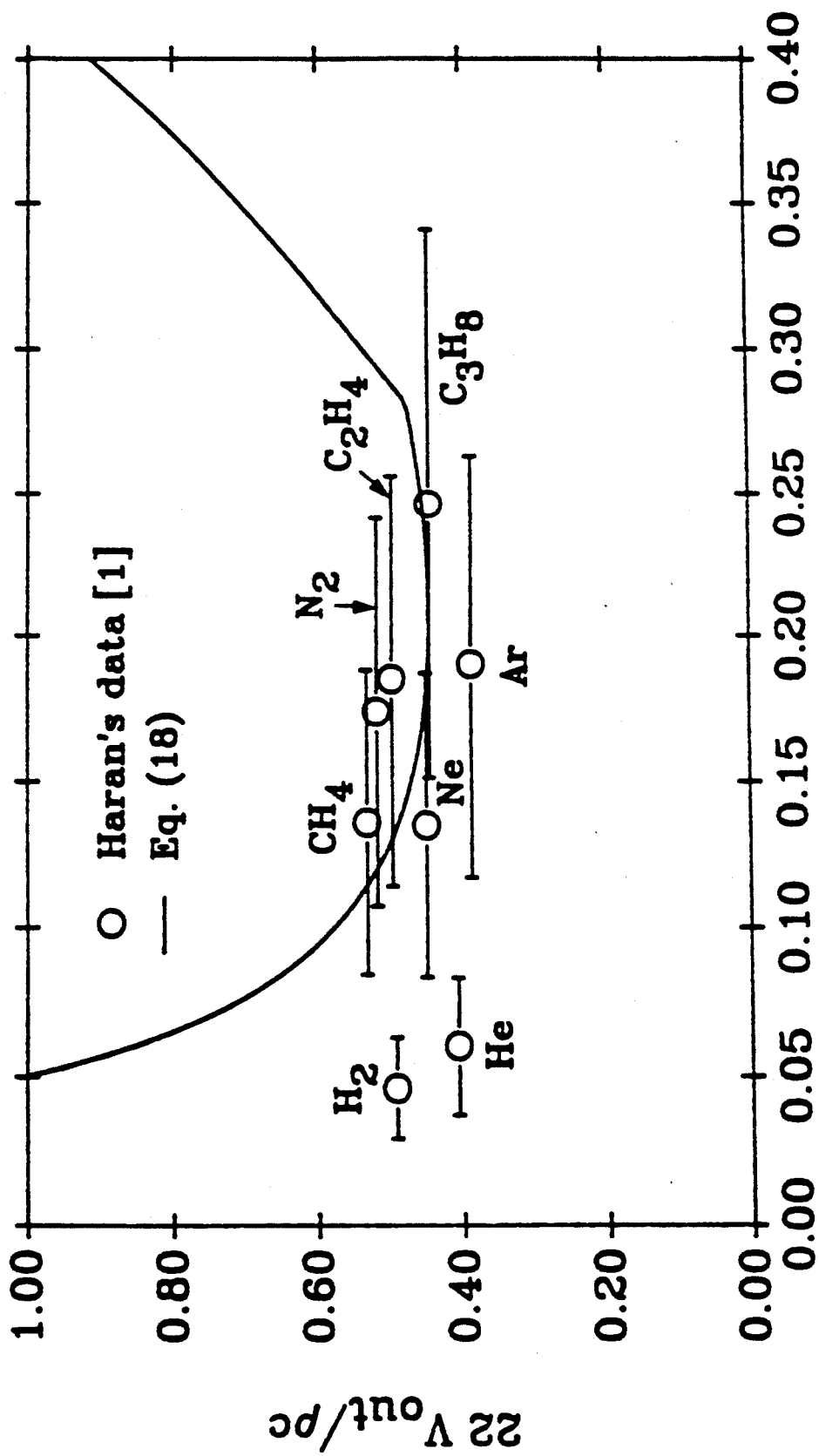
FIG. 8 uses the data of FIG. 7 and Table 1 and replots said data, according to the theory of this invention, as cell output/$\rho c$ as a function of $kL$, assuming a fixed frequency equal to 325 Hz. The data is shown compared to the predicted behavior according to the theory of this invention of a combined monopole and dipole source with $R_o/R=4$ represented by the trough-like shaped curve.

Haran used six evenly spaced frequencies between 200 and 450 Hz when experimenting with different gases using his prototype cell, which produces the non-linear response shown in FIG. 7. Haran verified that the ratio of the cell response in a chosen gas compared to that in air did not vary by more than 1% when the frequency was varied. This means that the quantity $F(kL,kL_o,kl)$ did not change with frequency. From Eq. 4, it follows that p must be proportional to $\rho c$. FIG. 8 shows that this is indeed the case.

The data in FIG. 8 shows the parameter (cell output)/$\rho c$ as a function of $kL$. The values of density were taken from the first mentioned publication of Haran and the values of c were taken at 300 K for all gases. In addition, it was assumed that $L=3$ cm and $f=325$ Hz to estimate $kL$. It was also assumed that $u_o$ is a constant over the range of frequencies 200–450 Hz, which is typical of loudspeakers when the loudspeaker is driven with constant voltage. The (cell output)/$\rho c$ appears to be a constant. However, our analysis shows that the pressure can only be proportional to $\rho$ for a dipole and to $\rho c^2$ for a monopole. We have found that we can now explain how a combined monopole and dipole source could produce a constant response over a range of values of $kL$ by plotting the combined analytical solution $$|p/\rho cu_o| = [p(\text{monopole}) + 3p(\text{dipole})]/\rho cu_o \quad \text{(Eq. 18)}$$

verses $kL$, using $L_o/L=4$. The ordinate has been scaled for the best fit with the data. Each data point at 325 Hz is extended by a horizontal line because the response is independent of frequency from 200 to 450 Hz. These lines are not error bars. Table 1 lists the values of the cell output, density, speed of sound and $kL$ values estimated using $L=3$ cm at $f=325$ Hz.

The combined solution is fairly successful in showing that the output has an extended constant zone, even though at the lower extreme, data from $H_2$ and He lie beyond the region that is flat. It is plausible that such a combination of sources could occur when a loudspeaker diaphragm is driven above the resonance frequency, which was much lower, i.e. between 60 and 85 Hz; see the first mentioned publication of Haran. It may also be possible to include higher-order poles, i.e. quadrupoles, etc., for a better fit with the data.

In the second mentioned publication of Haran, the densities of nitrogen at pressures from 0.2 to 20 atm were measured in an improved cell that behaves like a dipole and reported in FIG. 4 of the publication. The data appear to lie on a straight line passing through the origin in the form of cell output versus density or pressure. However, for a given gas at a fixed temperature, c hardly varies with pressure over the range of interest, up to 20 atm, and the cell output will be exactly proportional to $\rho$ whatever the value of $kL$. Testing a cell for linearity in density by pressurizing the cell is not sufficient because the parameter $kL$ remains fixed in that case. Accordingly, we have discovered that what is required is that the value $kL$ should be very small, the sound source must be dipole-like, and the apparatus small enough that resonances do not occur at very low values of $kL$.

The value of $kL$ in Haran's second paper was estimated by us to be 0.43 using $L=4$ cm and $f=600$ Hz. Frequency was not constant in Haran's experiments and values between 250 to 700 Hz were used with best results from 550 to 650 Hz. The densities of $H_2$ and Ar were also measured at atmospheric pressure by Haran in his improved cell and the results were discussed in his paper. We estimated that the values of $kL$ were 0.11 and 0.47 for $H_2$ and Ar, respectively.

As we have demonstrated by our analysis, $|p/\rho cu_o|$ is quite linear up to $kL=0.3$ for a dipole when $L_o/L=2$ as shown in FIG. 4. Since our analysis is for a spherical cell and does not include the effect of dissipation, $kL=0.47$ may be small enough for Haran's improved cell to produce linear results. Haran (per private communication) obtained good linear results for $H_2$, $CH_4$, $N_2$ and Ar with $f=630$ Hz at pressures from 0.82 to 9.2 atm using a smaller cell of dimensions reduced to one quarter of the size of Haran's improved cell.

In chemical or physical processes it is desirable, and often essential, to monitor and/or control the density of a gas or a mixture of gases. However, it is more difficult to measure gas density, especially on-line gas density, than it is to measure other quantities such as temperature and pressure. In this invention, gas density measurement is performed acoustically and on-line. The device is simple in design and operates with simple, readily available microphones. A small tube is either introduced into the process stream or, in an alternative embodiment where noise and temperature limitations can be avoided, flow is siphoned and bypassed through the tube. In one embodiment the small tube is excited by transducers at both ends thereof and sound pressure is detected a short distance away by a microphone located at a predetermined longitudinal distance along and on the tube's circumference. The process stream, or a portion thereof, is caused to be incident upon the small tube which is excited by transducers at both ends. The density of the gas, or mixture of gases, in the process stream, is measured by the detection of sound pressure with a microphone located at a predetermined longitudinal locations along the circumference of said tube.

In one embodiment the small tube is entirely within the process stream the density of which is to be measured. In another embodiment the small tube is entirely outside the main process stream. In still another embodiment the small tube is partly within and partly outside of the main process stream.

This invention, therefore, involves the use of sound or acoustic motion in a small tube which is excited either by a single transducer at a closed end of the small tube with the opposite end open, or by two transducers at both ends. The arrangement allows a measurement of the gas density to be made by the detection of sound pressure using a microphone located on the circumference at a suitable axial position.

Figure 9:
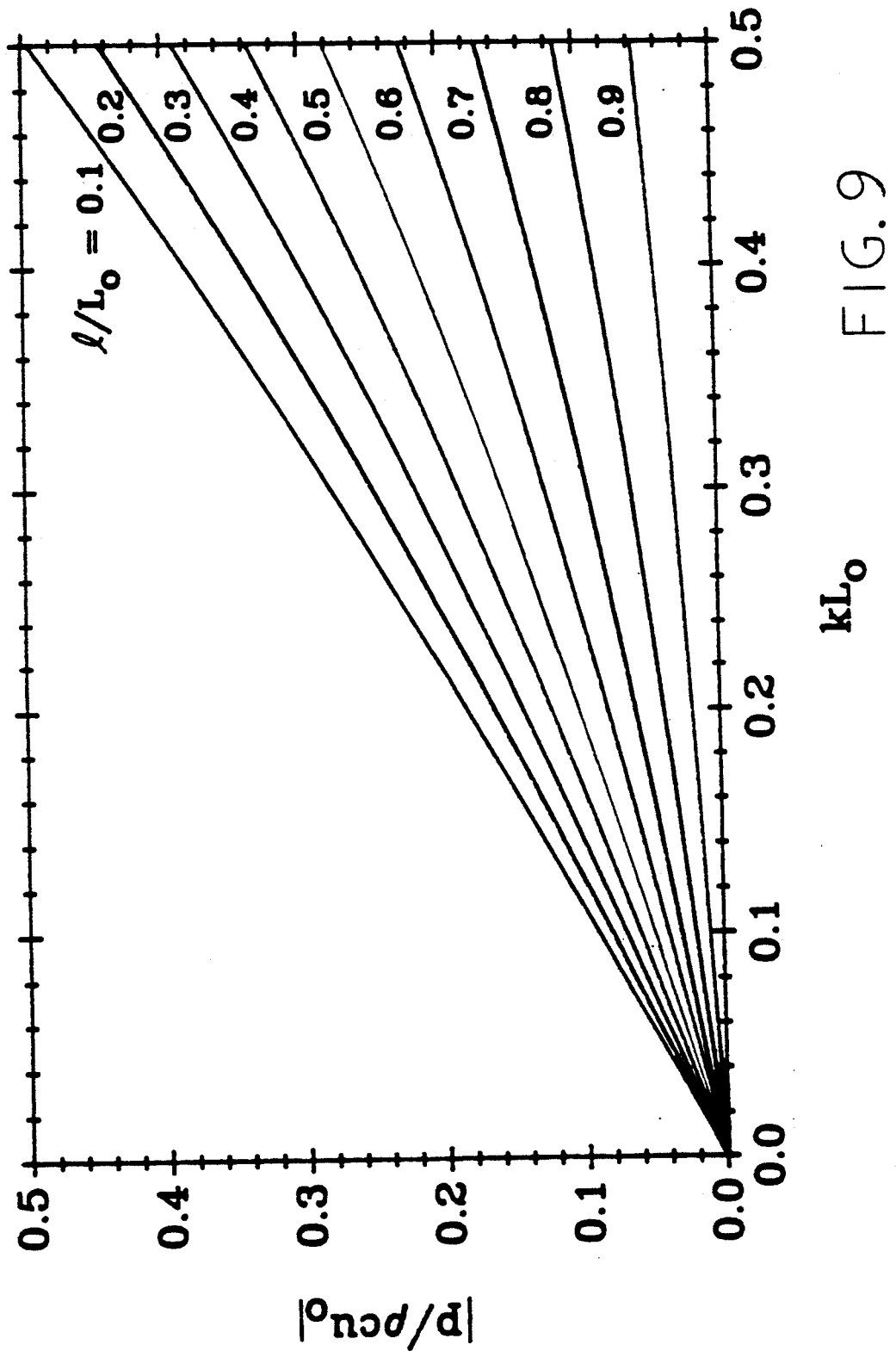
FIG. 9 is a graph of $|p/\rho c u_o|$ as a function of $kL_o$ for values of $l/L_o$ ranging from 0.1 for 0.9 for the schematic arrangement shown in FIG. 1.

As discussed above, the wave motion in a pipe where a sound source is at the closed end ($x=0$) and the opposite end ($x=L_o$) is open, will be a plane wave and the sound pressure is given by Eq. 17 above and shown in FIG. 6. More detailed results for small $kL_o$ are shown in FIG. 9 for various values of $1/L_o$ ranging from 0.1 to 0.9 for $kL_o$ from zero to 0.5. Because $|p/\rho c u_o|$ is linear in $kL_o$, $p \sim \rho u_o \omega L_o$. The density of the gas is then $$\rho \sim p/u_o \omega L_o. \qquad (\text{Eq. 19})$$

Since $u_o$ and $L_o$ are constants in a given system with $u_o$ being the transmitter excitation velocity at frequency $\omega$ or wave number $k=\omega/c$, the density of a gas can be obtained by measuring the sound pressure p at a given frequency at a sufficiently small value of $kL_o$. Since the line for a given value of $1/L_o$ in FIG. 9 is curved slightly there will be a small error if a linear approximation is used. However, the error will be within $\pm 1\%$ in most cases. Detailed error analysis will be discussed later.

Accordingly, there is provided by the principles of this invention an apparatus for measuring sound pressure values of a gas comprising a small tube having a first end and a second end, a gas inlet, and a small acoustical opening at a predetermined point between the first and second ends; transmitting means at one of the ends of the small tube, for transmitting a sound wave into the small tube, the transmitting means closing the small tube at said one of the ends; and sound receiver means located at the small acoustical opening for detecting sound pressure values at the predetermined point. The gas density is proportional to the sound pressure when the excitation frequency is small and below the first resonance frequency of the small tube.

In one embodiment the apparatus further comprises a second small tube having a first and second end, and a gas inlet. The axis of the second small tube is aligned parallel to the axis of the first mentioned small tube. This embodiment also has transmitting means at one of the ends of the second small tube for transmitting a sound wave into the second small tube. The transmitting means also serves to close the second small tube at its other ends.

In another embodiment the small tube has a gas outlet between the gas inlet and the second end. In still another embodiment the combination of the small tube, the transmitting-means and the sound receiver means has a dipole-like character. By the expression "dipole-like character" as used herein is meant that the pressure in the gas varies linearly or nearly linearly with the density of the gas in the sensor system, for example as illustrated in FIG. 9, as kL tends to zero.

In a further embodiment the apparatus further comprises means for converting sound pressure values into density values.

In one embodiment, where $L_o$ is the length of the small tube, L is the effective diameter of the transmitting means, l is the distance between the transmitting means and the small acoustical opening, and k is the wave number, the parameter $kL_o$ is no greater than about 0.4, the parameter kL is no greater than about 0.1, and the parameter kl is no greater than about 0.1. In another embodiment the frequency of the transmitting means is low enough to make the pressure of the gas linear or nearly linear with its density. In still another embodiment the transmitting means has a frequency from about 1 Khz to about 10 KHz.

In one embodiment the first end of the small tube is open and forms the gas inlet, and the transmitting means closes the second end of the small tube. In another embodiment the gas outlet of the small tube is proximate the transmitting means. In still another embodiment the gas outlet comprises an aperture through the small tube. In yet another embodiment the gas outlet comprises a plurality of small apertures extending radially through the small tube and spaced circumferentially around the small tube.

In one embodiment the length of the small tube is from about 5 to about 40 cm. In another embodiment the diameter of the small tube, the diameter of the small acoustical opening, the diameter of the transmitting means, and the diameter of the sound receiver means are approximately equal. In still another embodiment the diameter of the small tube, the diameter of the small acoustical opening, the diameter of the transmitting means, and the diameter of the sound receiver means are from about 0.5 to about 2 cm.

In one embodiment, where the gas is flowing, and the apparatus further comprises means for calibrating the sound pressure signal produced by the sound receiver means to compensate for a difference in temperature between the temperature of the small tube and the temperature of the flowing gas stream outside of the small tube.

In a further embodiment the apparatus further comprises second transmitting means for transmitting a sound wave into the small tube, and the second transmitting means also serve to close the other or first end of the small tube. In a still further embodiment the apparatus comprises means for exciting the first mentioned transmitting means and the second transmitting means in opposite phase.

In a further embodiment the apparatus also comprises a large conduit for receiving a flowing gas stream, means for introducing a portion of the flowing gas stream from the large conduit into the gas inlet of the small tube, and means for removing the portion of the flowing gas stream from the gas outlet of the small tube and introducing the removed portion of the flowing gas stream back into the large conduit. In one embodiment the small tube is positioned within the large conduit with the axis of the small tube parallel to the axis of the large conduit. In another embodiment the axis of the small tube is positioned obliquely or perpendicular to the axis of the large conduit, the first end of the small tube is open and forms the gas inlet, the transmitting means also serves to close the second end of the small tube, and the transmitting means, the sound receiver means, the small acoustical opening, the gas outlet and the second end of the small tube are positioned outside of the large conduit. In still another embodiment the first transmitting means closes one end of the small tube, and another or second transmitting means closes the other end of the small tube, and the small tube is positioned outside of the large conduit. In this embodiment small conduits connect the main process line to the inlet and outlet of the small tube.

There is also provided by the principles of this invention a method of determining the gas density of a flowing gas stream using sound pressure values comprising transmitting a sound wave into an acoustically shielded column of the flowing gas stream at a first location in the acoustically shielded column, detecting the sound pressure of the sound wave in the acoustically shielded column at a second location therein which is spaced a predetermined distance from the first location, thereby producing sound pressure values, and converting the sound pressure values into density values of the flowing gas stream thereby determining the density of the flowing gas stream. In one embodiment the method further comprises adjusting the length and the diameter of the acoustically shielded column, the predetermined distance between the second and first locations of the acoustically shielded column, and the frequency of the transmitted sound wave so that the gas density in the acoustically shielded column varies approximately linearly with the sound pressure at the predetermined distance whereat the sound pressure values are detected. In another embodiment the method further comprises adjusting both the frequency of the sound wave and the acoustically shielded column so that the combination has a dipole-like character. In a further embodiment the method also includes continuously introducing a portion of the flowing gas stream into an acoustically shielded column, and continuously removing the portion of the flowing gas stream from the acoustically shielded column thereby maintaining gas flow through the acoustically shielded column. In a still further embodiment the method also comprises calibrating the sound pressure values to compensate for a difference in temperature between the temperature of the acoustically shielded column and the temperature of the flowing gas stream outside the acoustically shielded column.

DESCRIPTION OF THE PREFERRED EMBODIMENTS

Figure 10:
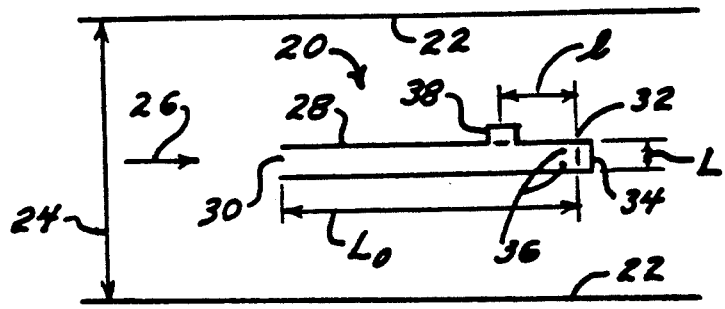
FIG. 10 depicts one embodiment of an in-line density sensor of this invention positioned in a process line for on-line gas density measurement.
Figure 11:
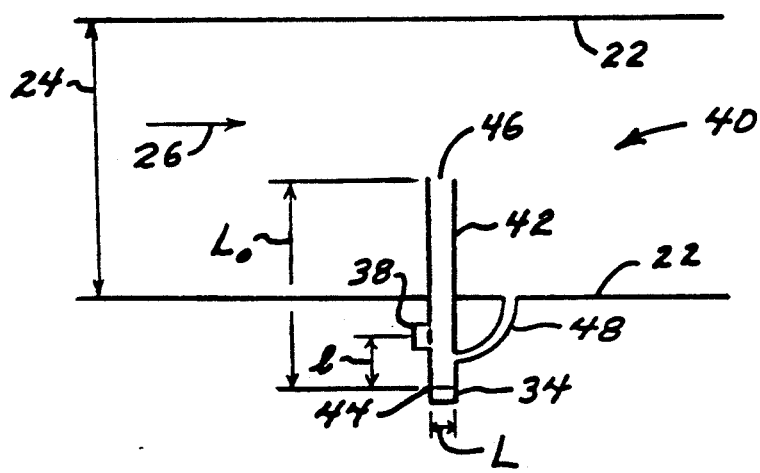
FIG. 11 depicts another embodiment of an in-line density sensor of this invention for minimizing the effect of flow noise wherein the small tube of the sensor is positioned partly in the process line while the transmitter and receiver are positioned outside of the process line.
Figure 12:
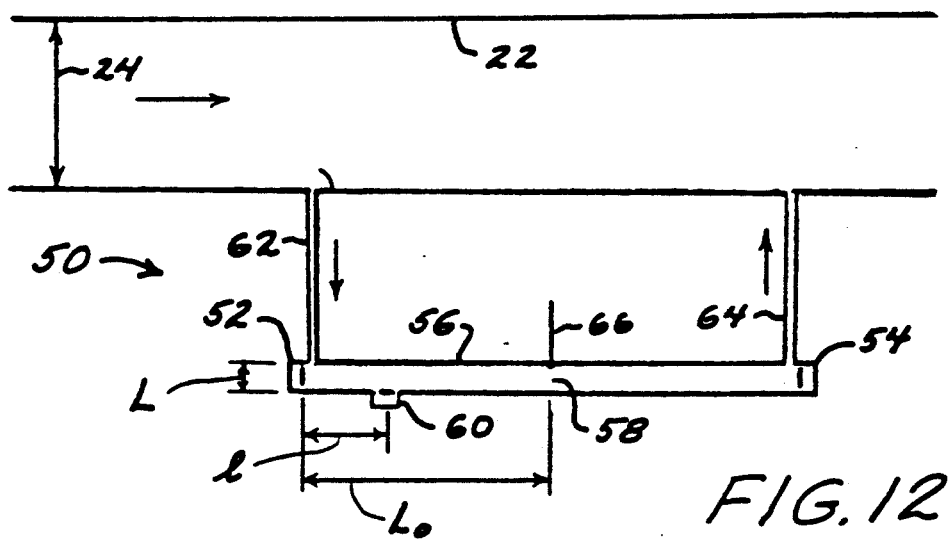
FIG. 12 depicts yet another embodiment on an in-line density sensor of this invention for minimizing the effect of noise and heat in which all the components of the sensor are positioned outside the process line and small conduits connect the gas inlet and outlet of the sensor to the process line.

FIGS. 10 and 11 show possible sensor applications in a process line, and in FIG. 12 an application away from the process line. In the embodiment shown in FIG. 10, a sensor 20 is located in process pipe line 22, having diameter 24, parallel to the direction of flow which is indicated by flow direction arrow 26. Sensor 20 comprises small tube 28 having a length $L_o$, diameter L, and an open end 30 which faces upstream, and a closed end 32 which contains sound transmitter transducer or microphone 34, having diameter L which is equal to the diameter of tube 28, operable for directing sound axially through small tube 28 to the open end 30. The gas whose density is to be determined flows into the open end of the small tube 28, then flows through the small tube, and exits the small tube through a plurality of small bleed holes 36 near transmitter 34. Receiver transducer or microphone 38 is spaced a distance l from transmitter transducer 34. One advantage of this embodiment of this invention is that the temperature of the gas inside small tube 28 is the same as the temperature in process line 22 thereby making data reduction relatively simple.

The same advantage can be achieved by using sensor embodiment 40 of this invention shown in FIG. 11. If the gas velocity is high, the signal to noise ratio in the embodiment of FIG. 10 may become poor because of flow noise and noise produced when the gas passes through the bleed holes 36. Furthermore the pressure in the small tube 28 will be higher than in the process stream due to the flow resistance of the small bleed holes which results in an increase in density measured by the sensor. These problems are alleviated in the embodiment shown in FIG. 11, wherein the axis of the small tube 42, which has a length $L_o$ and diameter L, is perpendicular to the axis of the process pipe line 22. The closed end 44 of small tube 42, transmitter transducer 34 and receiver transducer 38 are positioned outside of process line 22. Receiver transducer 38 is spaced predetermined distance l from transmitter transducer 34. The gas enters small tube 42 through open end 46. In place of the small bleed holes 36 of FIG. 10, sensor embodiment 40 has a small conduit 48 near the closed end 44 which allows the gas to flow from small tube 42 back into the main process pipe line 22. In noisier environments, a narrow band filter should be used.

For even noisier pipe line environments which generate low frequency noise the position of the sensors shown in FIGS. 10 and 11 may not be the best arrangement. Furthermore, there is also a maximum temperature limitation to which the transmitter transducer and receiver transducer may be exposed. Such noise and temperature limitations can be avoided by using a sensor, generally indicated by numeral 50, which is spaced away from the process pipe line with transmitters 52 and 54 at both ends of small tube 56 having diameter L as shown in FIG. 12. Transmitters 52 and 54, also having diameter L, are driven in opposite phases so that the sound pressure at the midpoint 58 or $L_o$ of small tube 56 will be zero. This is equivalent to the wave motion produced by a sound source at the closed end of a pipe having the other end open as described before with regard to FIGS. 10 and 11. The sound pressure is measured at a predetermined point longitudinally along the small tube 56 by receiver transducer 60, also having diameter L, positioned on the circumference of tube 56 at predetermined distance l from transmitter transducer 52. In this embodiment the flow of heat and noise into the sensor from the process line can be greatly minimized by the size and length of inlet and outlet conduits 62 and 64. If conduits 62 and 64 are made of a poor heat conducting material, such as stainless steel, the temperature of sensor 50 will be maintained at its recommended operational value. In the embodiment of FIG. 12, since the temperature in small tube 56 can be different from that in process line 22, the measured densities must be corrected for the temperature difference. The perfect gas law may be used for a first approximation, with the correct density $\rho_i$ being $$\rho_i = \rho_s T_s / T_i, \qquad \text{(Eq. 20)}$$

where subscripts "i" and "s" stand for "in the main process line", i.e. line 22, and "sensor", respectively. A temperature sensor 66 is located in the middle of the density sensor to minimize the effect of the presence of the temperature probe on the wave motion. If the surroundings are also very noisy, the density sensor can be acoustically insulated.

Figure 13:
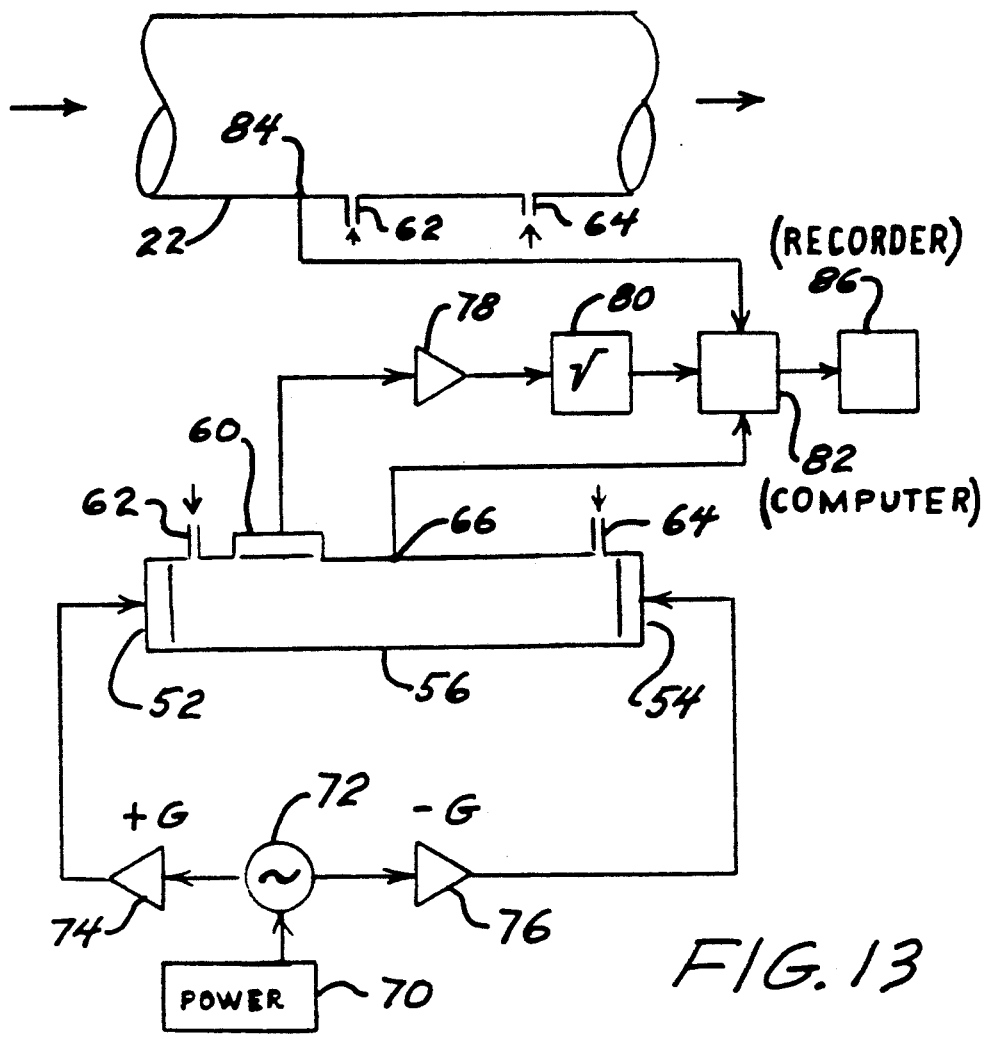
FIG. 13 is a block diagram for the density sensor of FIG. 12.

FIG. 13 is a block diagram for the density sensor of FIG. 12 in which power source 70 for wave oscillator 72 drives amplifiers 74 and 76 that have a 180° phase difference, which in turn drive transmitter transducers 52 and 54, respectively, causing positive and negative gain G. Receiver transducer 60 drives amplifier 78 which is connected to root-mean-square means 80. Means 80 transmits sound pressure data to computer 82. Thermocouples 66 and 84 transmit temperature data from small tube 56 and main process line 22, respectively, to computer 82. Computer 82 adjusts the sound pressure information from means 80 for temperature differences using temperature information from thermocouples 66 and 84, computes the gas density in main line 22 and transmits such density information to display recorder 86. A similar arrangement can be used for sensors 40 and 50, FIGS. 11 and 12, respectively, except that amplifier 76 and thermocouples 66 and 84 are not required since only one transmitter is required and temperature adjustment is not required.

FIG. 14, mentioned earlier, illustrates a dipole-like sensor system in which the principles of this invention can be used, if desired, in an enclosed environment to measure localized density within the environment. In this embodiment the open ends 90 and 92 of small tubes 94 and 96 of length $L_o$ are positioned in parallel relationship inside of enclosed environment 98 which contains gas 100. The other ends 102 and 104 of small tubes 94 and 96, respectively, contain sound transmitters 106 and 108, respectively, having effective diameter L. Transmitters 106 and 108 are driven 180° apart similar to that described for transmitters 52 and 54 of FIG. 12. Small tube 94 contains sound receiver 110 on the circumference at a predetermined distance, l, from transmitter 106.

A detailed error analysis of embodiments of this invention now follows. The gas density, in a single component gas, can vary only by changes in temperature and/or pressure, and in a mixture of gases, the gas density can also vary by changes in component volume ratios. The error analysis for a single component gas is the simpler of the two. Assuming that $L_o=10$ cm, $T_n=300$ K and $P_n=1$ atm where the subscript "n" refers to normal operating conditions, the value of $kL_o$ is 0.2 for $N_2$ if $f=112$ Hz. Since the speed of sound of most gases is almost independent of pressure, the value of $kL_o$ can vary only with the change of temperature. If $\pm 50\%$ of the change of the density is expected during processes, the temperature of $N_2$ gas varies from $2T_n/3$ to $2T_n$ at constant pressure. Since the speed of sound is proportional to the square root of T, the variation in the speed of sound in the gas at temperature T to the speed of sound at 300 K will be $0.816 < c/c_n < 1.414$. Therefore, the value of $kL_o$ can vary from 0.141 to 0.245. The error will be between $-0.75\%$ and $+0.66\%$ for $1/L_o=0.1$ when the linear approximation is used with a calibration at $kL_o=0.2$. The error increases slightly with increase of the value of $1/L_o$ and is between $-1\%$ and $+0.90\%$ for $1/L_o=0.9$. If the difference between the sound pressures is measured at two receivers located at different longitudinal positions along the small tube, the error can be reduced in half. Since the density changes in many processes are frequently much less than $\pm 50\%$, much less error will occur for such usages. Furthermore, if the excitation frequency for the transmitters is adjusted corresponding to the change in temperature by $$f=f_n(T/T_n)^{0.5}, \quad (Eq. 21)$$

the value of $kL_o$ remains the same and the error becomes negligible. Since the speed of sound of a mixture of gases depends on temperature as well as on the mean molecular weight and the specific heat ratio, more complicated steps are required to minimize the error. Nevertheless, the error will be quite small and will be acceptable for most on-line processes, even if only one microphone is used to measure density.

In general it is preferable that the diameter of the small tube be equal or nearly equal to the diameter of the transmitter transducer, L. In FIGS. 10, 11, 12 and 14 the diameters of the small tube and the transmitter transducers are the same.

In summary, we have shown that pressure at the receiver or cell output will be proportional to $\rho$ or $\rho c^2$ depending on the sound source type and operational and geometrical conditions. In order to measure gas density directly, the sound source should be dipole-like. The cell or sensor should be small and should be operated at a relatively low frequency so that the parameter kL is small, preferably less than about 0.3. For example, a small tube driven by a sound source at the closed end, situated in a flowing gas stream with a receiver transducer or microphone located a short distance from the closed end on the circumference of the small tube. Such a system provides a low cost density measurement cell of convenient design having high density measurement accuracy useful for in-line density determinations.

While the preferred embodiments of the present invention have been described, it should be understood that various changes, adaptations and modifications may be made thereto without departing from the spirit of the invention and the scope of the appended claims. It should be understood, therefore, that the invention is not to be limited to minor details of the illustrated invention shown in preferred embodiment and the figures and that variations in such minor details will be apparent to one skilled in the art.

Therefore it is to be understood that the present disclosure and embodiments of this invention described herein are for purposes of illustration and example and that modifications and improvements may be made thereto without departing from the spirit of the invention or from the scope of the claims. The claims, therefore, are to be accorded a range of equivalents commensurate in scope with the advance made over the art.

TABLE 1

| GAS | $\rho$ (kg/m³) | output (mV) | c (m/s) at 300 K | kL | $22 \cdot V_{out}/\rho c$ |
|---|---|---|---|---|---|
| $H_2$ | 0.102 | 3.01 | 1319 | 0.046 | 0.492 |
| He | 0.236 | 4.44 | 1020 | 0.060 | 0.406 |
| $CH_4$ | 0.742 | 8.06 | 450 | 0.136 | 0.531 |
| Ne | 0.960 | 8.87 | 453 | 0.135 | 0.449 |
| $N_2$ | 1.07 | 8.87 | 353 | 0.174 | 0.517 |
| $C_2H_4$ | 1.22 | 9.10 | 331 | 0.185 | 0.496 |
| Ar | 1.75 | 9.92 | 323 | 0.190 | 0.386 |
| $C_3H_8$ | 2.03 | 10.20 | 249 | 0.246 | 0.444 |

Assumed frequency = 325 Hz, L = 3 cm

What is claimed is:

1. An apparatus for measuring sound pressure values of a gas comprising:
    a small tube having a first end and second end, a gas inlet, and a small acoustical opening at a predetermined point between the first and second ends;
    transmitting means at one of the ends of the small tube, for transmitting a sound wave into the small tube, the transmitting means closing the small tube at said one of the ends; and
    sound receiver means located at the small acoustical opening, for detecting sound pressure values at the predetermined point.

2. The apparatus of claim 1, further comprising a second small tube having a first end and a second end, a gas inlet, the axis of the second small tube being parallel to the axis of the first mentioned small tube; and
    transmitting means at one of the ends of the second small tube, for transmitting a sound wave into the second small tube, for transmitting means closing the second small tube at said one of its ends.

3. An apparatus for measuring sound pressure values of a gas comprising:
    a small tube having a first end and second end, a gas inlet proximate the first end, a gas outlet between the gas inlet and the second end, and a small acoustical opening at a predetermined point between the first and second ends;

transmitting means at one of the ends of the small tube, for transmitting a sound wave into the small tube, the transmitting means closing the small tube at said one of the ends; and sound receiver means located at the small acoustical opening, for detecting sound pressure values at the predetermined point.

4. The apparatus of claim 3, wherein the combination of the small tube, the transmitting means and the sound receiver means has a dipole-like character.

5. The apparatus of claim 3, further comprising means for converting sound pressure values into density values.

6. The apparatus of claim 3, where $L_o$ is the length of the small tube, where L is the effective diameter of the transmitting means, where l is the distance between the transmitting means and the small acoustical opening, and k is the wave number, and wherein the parameter $kL_o$ is no greater than about 0.4, wherein the parameter kL is no greater than about 0.1, and wherein the parameter kl is no greater than about 0.1.

7. The apparatus of claim 3, wherein the transmitting means has a frequency from about 1 KHz to about 10 KHz.

8. The apparatus of claim 3, wherein the first end of the small tube is open and forms the gas inlet, and the transmitting means closes the second end of the small tube.

9. The apparatus of claim 3, wherein the gas outlet of the small tube is proximate the transmitting means.

10. The apparatus of claim 3, wherein the gas outlet comprises an aperture through the small tube.

11. The apparatus of claim 3, wherein the gas outlet comprises a plurality of small apertures extending radially through the small tube and spaced circumferentially around the small tube.

12. The apparatus of claim 3, wherein the length of the small tube is from about 5 to about 40 cm.

13. The apparatus of claim 3, wherein the diameter of the small tube, the diameter of the small acoustical opening, the diameter of the transmitting means, and the diameter of the sound receiver means are approximately equal.

14. The apparatus of claim 3, wherein the diameter of the small tube is from about 0.5 to about 2 cm, wherein the diameter of the small acoustical opening is from about 0.5 to about 2 cm, wherein the diameter of the transmitting means is from about 0.5 to about 2 cm, and wherein the diameter of the sound receiver means is from about 0.5 to about 2 cm.

15. The apparatus of claim 3, wherein the gas is flowing.

16. The apparatus of claim 15, wherein the sound receiver means produces a sound pressure signal, and further comprising calibrating means for adjusting the sound pressure signal produced by the sound receiver means to compensate for a difference in temperature between the temperature of the small tube and the temperature of the flowing gas outside of the small tube.

17. The apparatus of claim 3, wherein the transmitting means closes the second end of the small tube, and further comprising second transmitting means for transmitting a sound wave into the small tube, the second transmitting means closing the first end of the small tube.

18. The apparatus of claim 17, further comprising driving means for exciting the first mentioned transmitting means and the second transmitting means in opposite phase.

19. An apparatus for measuring sound pressure values of a flowing gas stream, the apparatus comprising:

a large conduit for receiving a flowing gas stream;

a small tube having a first end and a second end, a gas inlet proximate the first end, a gas outlet between the gas inlet and the second end, and a small acoustical opening at a predetermined point between the first and second ends;

means for introducing a portion of the flowing gas stream for the large conduit into the gas inlet of the small tube;

means for removing the portion of the flowing gas stream from the gas outlet of the small tube and introducing the removed portion of the flowing gas stream back into the large conduit;

transmitting means at one of the ends of the small tube, for transmitting a sound wave into the small tube, the transmitting means closing the small tube at said one of the ends; and sound receiver means located on the outside of the small tube at the small acoustical opening, for detecting the sound pressure values at the predetermined point.

20. The apparatus of claim 19, wherein the small tube is positioned within the large conduit with the axis of the small tube being parallel with the axis of the large conduit, and wherein the first end of the small tube is open and forms the gas inlet, and the transmitting means closes the second end of the small tube.

21. The apparatus of claim 19, wherein the axis of the small tube is positioned perpendicular to the axis of the large conduit, wherein the first end of the small tube is open and forms the gas inlet, wherein the transmitting means closes the second end of the small tube, wherein the gas outlet is proximate the transmitting means and comprises an aperture through the small tube, and wherein the transmitting means, the sound receiver means, the small acoustical opening, the gas outlet and the second end of the small tube are positioned outside of the large conduit.

22. The apparatus of claim 19, wherein the transmitting means closes the second end of the small tube, and further comprising second transmitting means for transmitting a sound wave into the small tube, the second transmitting means closing the first end of the small tube, and wherein the small tube is positioned outside of the large conduit.

23. A method of transmitting the gas density of a flowing gas stream using sound pressure values comprising:

a. transmitting a sound wave into an acoustically shielded column of the flowing gas stream at a first location in the acoustically shielded column;

b. detecting the sound pressure of the second wave in the acoustically shielded column at a second location therein which is spaced a predetermined distance from the first location, thereby producing sound pressure values; and c. converting the sound pressure values into density values of the flowing gas stream thereby determining the density of the flowing gas stream.

24. The method of claim 23, further comprising adjusting the length and the diameter of the acoustically shielded column, the predetermined distance between the second and first locations of the acoustically shielded column, and the frequency of the transmitted sound wave so that the gas density in the acoustically shielded column varies approximately linearly with the sound pressure at the predetermined distance whereat the sound pressure values are detected.

25. The method of claim 23, further comprising adjusting the frequency of the sound wave so that the acoustically shielded column has a dipole-like character.

26. A method of determining the gas density of a flowing gas stream using sound pressure values comprising:
   a. continuously introducing a portion of the flowing gas stream into an acoustically shielded column;
   b. continuously removing the portion of the flowing gas stream from the acoustically shielded column thereby maintaining gas flow through the acoustically shielded column;
   c. transmitting a sound wave into the acoustically shielded column at a first location therein;
   d. detecting the sound pressure of the sound wave in the acoustically shielded column at a second location therein which is spaced a predetermined distance from the first location, thereby producing sound pressure values; and
   e. converting the sound pressure values into density values of the flowing gas stream thereby determining the density of the flowing gas stream.

27. The method of claim 26, further comprising calibrating the sound pressure values to compensate for a difference in temperature between the temperature of the acoustically shielded column and the temperature of the flowing gas stream outside the acoustically shielded column.

* * * * *